(12) United States Patent
Hayase et al.

(10) Patent No.: US 11,827,658 B2
(45) Date of Patent: Nov. 28, 2023

(54) PEROVSKITE COMPOUND AND PHOTOCONVERSION DEVICE USING THE SAME

(71) Applicant: The University of Electro-Communications, Tokyo (JP)

(72) Inventors: Shuzi Hayase, Fukuoka (JP); Nozomi Ito, Fukuoka (JP)

(73) Assignee: The University of Electro-Communications, Tokyo (JP)

( * ) Notice: Subject to any disclaimer, the term of this patent is extended or adjusted under 35 U.S.C. 154(b) by 757 days.

(21) Appl. No.: 16/961,397

(22) PCT Filed: Jan. 11, 2019

(86) PCT No.: PCT/JP2019/000798
§ 371 (c)(1),
(2) Date: Jul. 10, 2020

(87) PCT Pub. No.: WO2019/139153
PCT Pub. Date: Jul. 18, 2019

(65) Prior Publication Data
US 2020/0361968 A1    Nov. 19, 2020

(30) Foreign Application Priority Data
Jan. 15, 2018    (JP) .................... 2018-004523

(51) Int. Cl.
*C07F 7/22* (2006.01)
*C07F 7/30* (2006.01)
*H10K 30/80* (2023.01)
*H10K 30/20* (2023.01)
*C07C 211/62* (2006.01)

(52) U.S. Cl.
CPC .......... *C07F 7/2208* (2013.01); *C07C 211/62* (2013.01); *C07F 7/30* (2013.01); *H10K 30/20* (2023.02); *H10K 30/80* (2023.02); *Y02E 10/549* (2013.01)

(58) Field of Classification Search
CPC .......... C07F 7/2208; C07F 7/30; H10K 30/80; H10K 30/20; Y02E 10/549; C07C 211/62
See application file for complete search history.

(56) References Cited

U.S. PATENT DOCUMENTS

2018/0066383 A1    3/2018    Bakr et al.

FOREIGN PATENT DOCUMENTS

| CN | 105218594 | 1/2016 |
|---|---|---|
| WO | 2016/151535 | 9/2016 |

OTHER PUBLICATIONS

K. Yamamoto, S. Iikubo,* J. Yamasaki, Y. Ogomi, and S. Hayase, "Structural Stability of Iodide Perovskite: A Combined Cluster Expansion Method and First-Principles Study", The Journal of Physical Chemistry, C 2017 121 (50), 27797-27804 (Year: 2017).*

(Continued)

*Primary Examiner* — Ermias T Woldegeorgis
(74) *Attorney, Agent, or Firm* — IPUSA, PLLC (57) ABSTRACT

A Pb-free Sn-halide Perovskite solar cell with improved photoelectric conversion efficiency is provided. A solar cell uses a perovskite compound represented by $ABX_3$ where A is a cation, B is a metal, and X is a halogen, wherein each of A, B and X may be composed of a plurality of elements, and B includes Sn and Ge.

20 Claims, 7 Drawing Sheets

(56) References Cited

OTHER PUBLICATIONS

M. Saliba et al., "Cesium-containing triple cation perovskite solar cells: improved stability, reproducibility and high efficiency", Energy Environ. Science, 2016, 9, pp. 1989-1997.
Ming-Gang Ju et al., "Lead-free mixed tin and germanium perovskites for photovoltaic application", Journal of the American Chemical Society, May 24, 2017, 139(23), pp. 8038-8043.
International Search Report dated Apr. 9, 2019 with respect to PCT/JP2019/000798.
Office Action dated Nov. 15, 2022 with respect to the corresponding Japanese patent application No. 2019-564770.
K. Yamamoto et al., "Structural Stability of Iodide Perovskite: A Combined Cluster Expansion Method and First-Principles Study", J. Phys. Chem. C, 121, pp. 27797-27804, Nov. 30, 2017.

\* cited by examiner

PEROVSKITE COMPOUND AND PHOTOCONVERSION DEVICE USING THE SAME

TECHNICAL FIELD

The present invention relates to a perovskite compound, a photoconversion device using the same, and solar cell and photosensor provided with the photoconversion device.

BACKGROUND ART

In recent years, perovskite compounds have attracted attention because of their extremely high photoconversion efficiency. A perovskite solar cell using such perovskite compounds has a solid hole transport layer formed of a perovskite compound, in place of the dye-carrier of a conventional solid-type dye-sensitized solar cell. The perovskite solar cell has a remarkable feature that can achieve higher conversion efficiency than a conventional liquid electrolyte using dye molecules.

The perovskite compound layer provided in a perovskite solar cell is generally fabricated by spin-coating a perovskite compound dissolved in an organic solvent over a template layer which is, for example, a porous titania film, to form perovskite thin films with different crystalline natures.

Note that dye-sensitized solar cells, organic solar cells, and perovskite solar cells are typical printable solar cells. Conventional perovskite solar cells have a Pb-halide perovskite layer as a photo-absorption layer. Such a Pb-halide perovskite solar cell has a small cell area, but one with the photoelectric conversion efficiency exceeding 20% is reported. (See Non-patent document 1 presented below). This conversion efficiency is close to that of commercially available inorganic solar cells. In addition, although at an oral presentation, it is officially reported that a photoelectric conversion efficiency of 15% is achieved by a cell area of 1 $cm^2$.

In general, $CH_3NH_3PbI_3$ is used as a halide perovskite compound. The absorption edge in the light absorption spectrum of this halide perovskite compound is 800 nm. If photoelectric conversion up to 900 nm is achieved, the efficiency can be improved without lowering the open circuit voltage. For example, assuming that the voltage loss from the theoretical open-circuit voltage of the perovskite solar cell is 0.3 V, and that the light from the visible range to 900 nm can be photoelectrically converted under the conditions of fill factor (FF) of 0.7 and incident Photon to current efficiency (IPCE) of 0.8, then the conversion efficiency of 20.4% will be achieved. However, since conventional Pb-containing perovskite solar cells such as $CH_3NH_3PbI_3$ solar cells have high environmental risk, development of Pb-free perovskite solar cells is desired.

At present, a Sn halide perovskite solar cell using a tin-based halide perovskite compound is known as a Pb-free perovskite solar cell. It is known that a Sn halide perovskite compound has a light absorption spectrum over 1200 nm; however, the detailed physical properties have not been clarified yet. Further, the photoelectric conversion efficiency of the solar cell using a Sn halide perovskite compound is insufficient, and improvement of the photoelectric conversion efficiency has been demanded.

PRIOR ART DOCUMENTS

Non-Patent Document 1:
M. Saliba, T. Matsui; J. Y. Seo, K. Domanski, J. P. Correa-Baena, M. K. Nazeeruddin, S. M. Zakeeruddin, W. Tress, A. Abate, A. Hagfeldt and M Gratzel, Cesium-containing triple cation perovskite solar cells: improved stability, reproducibility and high efficiency. Energy Environ. Sci., 2016, 9, pp. 1989-1997

SUMMARY OF THE INVENTION

Technical Problem to be Solved

An objective of the invention is to provide a Pb-free Sn halide perovskite compound with an improved photoelectric conversion efficiency, and a device using the same, such as a solar cell.

Technical Solutions

In view of the above-described technical problems, the inventors made thorough studies and investigations, and found that in a perovskite compound represented by general formula $ABX_3$ (where A is a cation, B is a metal, and X is a halogen), the photoelectric conversion efficiency is greatly improved using Sn and Ge for the B site, compared with a conventional configuration solely using Sn as the metal B. Thus, the invention was conceived.

In particular, the invention includes the following features.

[1] A perovskite compound comprising a $ABX_3$ (where A is a cation, B is a metal, X is a halogen, and A, B and X each may be composed of one or more elements), wherein B includes Sn and at least one metal selected from groups 12, 13, 14, 15 and 16 of the periodic table excluding Sn and Pb.

[2] The perovskite compound as described in the above item [1], wherein B includes Sn and Ge.

[3] The perovskite compound as describe in the above item [2], wherein B consists of Sn and Ge.

[4] The perovskite compound as described in any one of the above items [1] to [3], wherein the composition of Sn in B is 70% to 99.5% and the composition of the other metal(s) in B is 0.5% to 30%.

[5] The perovskite compound as described in the above item [2] or [3], wherein the composition of Sn in B is 70% to 99.5% and the composition of Ge is 0.5% to 30%.

[6] The perovskite compound as described in the above item [5], wherein the composition of Sn in B is 80% to 99% and the composition of Ge in B is 1% to 20%.

[7] The perovskite compound as described in any one of the above items [1] to [6], wherein A is an organic amine or an alkali metal.

Other inventions are as follows.

[8] A photoelectric conversion device having a photo-absorption layer containing the perovskite compound as described in any one of the above items [1] to [7].

[9] A photoelectric conversion device having a photo-absorption layer containing the perovskite compound as described in the above item [6].

[10] The photoelectric conversion device as described in the above item [8] or [9], wherein the photo-absorption layer is provided between a hole transport layer and an electron transport layer.

[11] A solar cell having the photoelectric conversion device as described in any one of the above items [8] to [10].

[12] A photosensor having the photoelectric conversion device as described in any one of the above items [8] to [10].

Advantageous Effect of the Invention

The perovskite compound of the present invention has a high photoelectric conversion efficiency and is applicable to solar cells and photosensors.

BEST MODE FOR IMPLEMENTING THE INVENTIONS

[Perovskite Compound]

The perovskite compound of the present invention is a compound composed of $ABX_3$ (A: cation, B: metal, X: halogen), in which B includes Sn, and at least one metal selected from groups 12, 13, 14, 15, and 16 of the periodic table except for Sn and Pb. Each of A, B, and X may be one element, or composed of multiple elements. When represented by $A-B-X_3$, the perovskite compound has a cubic structure in which a metal B is located at the center of the cube, cations A are located at the respective apexes, and halogens X are located at the face centers.

The perovskite compound of the invention does not contain Pb, which has a high environmental risk, and it has a high photoelectric conversion efficiency. The photoelectric conversion efficiency can be maintained even when left exposed to the air, exhibiting high stability in the open air. Accordingly, it is suitable for the material of a photoelectric conversion device used in solar cells, photosensors, or the like. Specifically, the perovskite compound of the invention can be applied to a photo-absorption layer that absorbs light and converts it into charges (holes and electrons).

The metal B in the perovskite compound of the invention includes Sn and other metals as described above. Examples of the other metals include Zn, Ga, Ge, As, Cd, In, Sb and Te, among which Ge is particularly preferable. That is, the metal B preferably includes Sn and Ge, and is preferably composed of these two elements.

The compositions of Sn and other elements of metal B can be appropriately adjusted within a range where the effect of the invention is achieved. Preferably, the percent composition of Sn is equal to or greater than 70%, more preferably equal to or greater than 80%, and still more preferably equal to or greater than 85%. It is yet more preferably that the composition of Sn is equal to or greater than 90%, and most preferably equal to or greater than 92%. The content of other metals (especially Ge) is preferably equal to or greater than 0.5%, more preferably equal to or greater than 1%, and still more preferably equal to or greater than 3%. Particularly, it is preferable that the Sn content is 70 to 99.5% and that the content of other metals is 0.5 to 30%. It is more preferable that the Sn content is 80 to 99% and that the content of other metals is 1 to 20%. It is still more preferable that the Sn content is 85 to 99% and the content of other metals is 1 to 15%. It is particularly preferable that the Sn content is 90 to 97% and that the content of other metals is 3 to 10%. It is most preferable that the Sn content is 92 to 97% and the content of other metals is 3 to 8%.

Examples of the cation A include alkali metals and organic amines, and organic amines are preferable. Cesium is preferred as the alkali metal. Examples of the organic amine include a primary, secondary, tertiary, or quaternary organic ammonium compound, which may have a heterocycle containing N or a carbon ring. Specifically, methylammonium (MA), formamidinium (FA:$NH_2CH=NH^{2+}$), ethylenediammonium (EA), pyrazinium, 2-phenylethylammonium (PEA), benzylamine, 4-fluoroaniline, 4-fluorobenzylamine, 4-fluorophenethylamine, phenethylammonium, or combinations of two or more of these may be used. Among these, methylammonium (MA) and formamidinium (FA) are preferable from the viewpoint of a three-dimensional structure with a wide absorption spectrum, and a combination thereof is particularly preferable.

Examples of the halogen X include F, Cl, Br, I, or the like, and two or more of them may be used in combination. Among these, I is preferable from the viewpoint of carrier mobility.

The perovskite compound ($ABX_3$) of the present invention can be produced by, for example, dissolving AX and $B^1X_2$ in an organic solvent and forming a film using the solution. For preparing a perovskite compound of $AB^1B^2X_3$, for example, an $AB^1X_3$ precursor solution in which AX and $B^1X_2$ are dissolved in an organic solvent and an $AB^2X_3$ precursor solution in which AX and $B^2X_2$ are dissolved in an organic solvent are mixed at a predetermined ratio to form a film.

The organic solvent is not particularly limited as long as it can dissolve the precursor substance. For example, N,N-dimethylformamide (DMF), dimethylsulfoxide (DMSO), γ-butyrolactone, dimethylacetamide (DMA), 1,3-dimethyl-2-imidazolidinone, acetylacetone, tert-butylpyridine, dimethylethyleneurea (DMI), dimethylpropyleneurea (DMU), and tetramethylurea (TMU) can be used, and two or more of these may be used in combination. Among these, N,N-dimethylformamide (DMF) and dimethylsulfoxide (DMSO) are preferable from the viewpoint of solubility.

The film deposition process for forming the film of the precursor solution is not particularly limited, and either coating or vapor deposition such as vacuum evaporation may be employed. Coating may be preferable because a film can be easily formed in a short time. Any known coating method can be used, including dip coating, die coating, bar coating, spin coating, offset method, spray coating, and printing. Among these, spin coating is preferable from the viewpoint of uniformity of a thin film and a dense polycrystalline structure.

The perovskite compound of the invention can be suitably used as a material of photo-absorption layers of photoelectric conversion devices. In other words, the photoelectric conversion device of the invention has a photo-absorption layer containing the above-described perovskite compound.

The configuration of the photoelectric conversion device of the invention is not particularly limited as long as it includes at least a first electrode, a second electrode, and a photo-absorption layer provided between the first electrode and the second electrode, which are provided on or above a substrate. The device may include one or more functional layers in addition to the photo-absorption layer. Such functional layers include, but are not limited to, a hole transport layer, an electron transport layer, a hole blocking layer, an electron blocking layer, a buffer layer, or the like.

Figure 1:
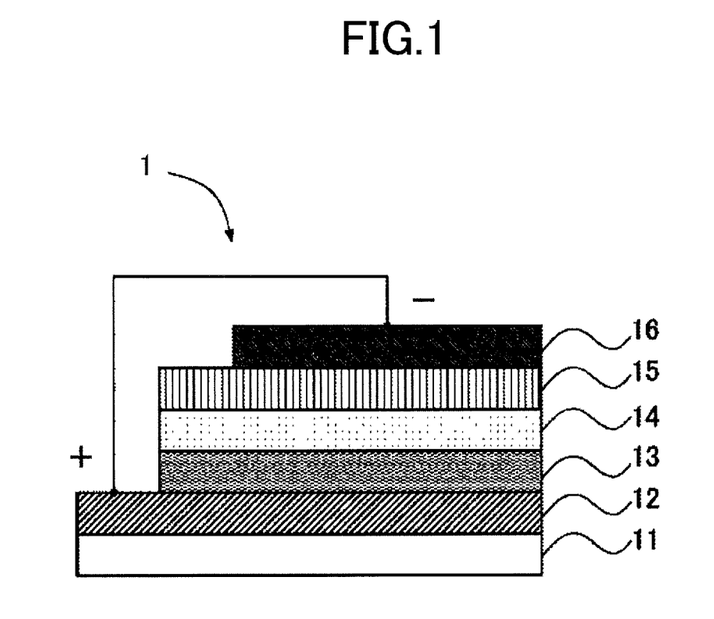
FIG. 1 is a schematic diagram of a photoelectric conversion device (one example) of an invention.

FIG. 1 illustrates an example of the photoelectric conversion device of an invention. In FIG. 1, a photoelectric conversion device 1 according to an embodiment of the invention includes a substrate 11, a first electrode 12, a hole transport layer 13, a photo-absorption layer 14, an electron transport layer 15, and a second electrode 16 stacked in this order from the bottom. In this photoelectric conversion device 1, the first electrode 12 serves as a positive electrode that collects holes, and the second electrode 16 serves as a negative electrode that collects electrons.

The photoelectric conversion device of the invention may have an inverted structure in which the positions of the hole transport layer 13 and the electron transport layer 15 are swapped with respect to the structure of FIG. 1. Namely, the substrate 11, the first electrode 12, the electron transport layer 15, the photo-absorption layer 14, the hole transport layer 13, and the second electrode 16 may be stacked in this order for the inverted configuration. In this case, the first electrode 12 serves as a negative electrode to collect electrons, and the second electrode 16 serves as a positive electrode to collect holes.

Next, each member of the photoelectric conversion device (with a normal structure) will be described below.

(Substrate)

The substrate is not particularly limited as long as it is transparent or semi-transparent so that light can be transmitted. Examples of the substrate include glass, plastic, or quartz substrates. Plastics include polyethylene naphthalate, polyethylene terephthalate, polycarbonate, polyolefin, etc.

(First Electrode (Positive Electrode))

The material of the first electrode is not particularly limited as long as it is transparent or semi-transparent, and a conductive inorganic compound, a conductive metal oxide, a conductive polymer, or a mixture thereof can be used. Specific examples of the material of the first electrode include a metal oxide such as indium tin oxide (ITO), indium zinc oxide (IZO), aluminum-doped zinc oxide (AZO), zinc oxide (ZnO), tin oxide ($SnO_2$), or titanium oxide ($TiO_2$), as well as conductive polymers. Two or more of these materials may be combined to form the first electrode.

(Second Electrode (Negative Electrode))

For the second electrode, metals, alloys, carbon materials and mixtures thereof can be used, in addition to the materials exemplified for the first electrode. For example, gold, silver, platinum, copper, aluminum, titanium or the like can be used for the second electrode. Two or more of these materials may be used in combination.

(Photo-Absorption Layer)

The photo-absorption layer contains a perovskite compound of the invention. When the light is incident on the photo-absorption layer from the substrate, the perovskite compound in the layer is photoexcited and spatially separated charge carriers (holes and electrons) are generated. Of these charge carriers, holes are diffused toward the hole transport layer and collected at the first electrode, while electrons are diffused toward the electron transport layer and collected at the second electrode, and a potential difference (electromotive force) is generated between the first electrode and the second electrode. The thickness of the photo-absorption layer is preferably 10 to 1000 nm, more preferably 100 to 500 nm, and further preferably 200 to 400 nm. In the photo-absorption layer containing a perovskite compound of the invention, Ge is localized near the interfaces (particularly at the interface with the hole transport layer) (see FIG. 7). Accordingly, charge injections into the hole transport layer and the electron transport layer are promoted. The layer is a flat film with few pinholes (see FIG. 8 and FIG. 9). Furthermore, oxidation due to the hole transport layer (PEDOT:PSS which is a hydrophilic carrier layer) can be prevented.

(Hole Transport Layer)

For the hole transport layer, a material having a function of transporting the holes injected from the photo-absorption layer toward the first electrode can be used. Examples of the material for the hole transport layer include, for example, poly(3,4-ethylenedioxythiophene):poly(4-styrenesulfonate) (abbreviated as PEDOT:PSS), NiO, $V_2O_5$, $MoO_3$, etc. Among these, two or more materials may be used in combination. The hole transport layer may be composed of a single layer or multiple layers, and it may have a hole injecting function or an electron blocking function.

(Electron Transport Layer)

For the electron transport layer, a material having a function of transporting electrons injected from the photo-absorption layer toward the second electrode can be used. Examples of the material used for the electron transport layer include, for example, CH fullerene, higher fullerenes, bathocuproine (BCP) or the like, and two or more of them may be used in combination. The electron transport layer may be composed of a single layer or multiple layers, and it may have a hole blocking function or a buffer function.

When light such as sunlight is incident on the photoelectric conversion device from the substrate side, the perovskite compound contained in the photo-absorption layer is excited and charge carriers (holes and electrons) are generated. The holes are collected into the positive electrode, while the electrons are collected into the negative electrode, and an electromotive force is generated between the positive electrode and the negative electrode. By connecting the positive electrode and the negative electrode between which the electromotive force has been generated, with a conductor, a current flows from the positive electrode to the negative electrode. Thus, the photoelectric conversion device of the invention can be applied to a solar cell, a photosensor, or the like.

The photoelectric conversion device of the present invention has a high photoelectric conversion efficiency, compared with a conventional photoelectric conversion device using a perovskite compound containing only Sn in the B site. Because no Pb is contained, a safe photoelectric conversion device is achieved. Further, the photoelectric conversion efficiency can be maintained high even when the device is left in the open air. The photoelectric conversion device of the invention may be used as a single device, or alternatively, as a device of tandem type by stacking a plurality of devices.

EXAMPLES

Some examples of the invention are described below; however, the scope of the invention is not limited to these examples.

Example 1

A photoelectric conversion device was fabricated using a perovskite compound $CH_3NH_3SnGeI_3$ ($MASnGeI_3$) according to the invention, and its characteristics were evaluated.

<Preparation of Perovskite Film>

Deposition of a perovskite film was performed in a nitrogen-purged glove box.

A $MASnI_3$ precursor solution was prepared by dissolving $SnI_2$ (596 mg), $SnF_2$ (25 mg) and MAI (64 mg) in DMF (1773 µL) and DMSO (227 µL). A $MAGeI_3$ precursor solution was also prepared by dissolving $GeI_2$ (131 mg) and MAI (16 mg) in DMF (500 µL). Finally, the $MASnGeI_3$ precursor solution was prepared by mixing the $MASnI_3$ precursor solution and the $MAGeI_3$ precursor solution at a volume ratio of 4 to 1 (4:1).

The precursor solution was filtered with a 0.2 µm filter and spin-coated on the substrate (PEDOT:PSS) at 5000 rpm for 50 seconds. In the spin coating process, toluene acting as an anti-solvent was dropped onto the substrate before the perovskite solution was completely dried in order to flatten the surface of the perovskite. After completion of spin coating, the perovskite film was annealed on a hot plate at 70° C. for 10 minutes. The composition of the fabricated perovskite film is $MASnGeI_3$.

For a comparison, the $MASnI_3$ precursor solution of Example 1 was used to prepare a $MASnI_3$ perovskite film (Comparative film 1), and the $MAGeI_3$ precursor solution of Example 1 was used to prepare a $MAGeI_3$ perovskite film (Comparative film 2).

<Device Fabrication>

An FTO-coated glass substrate (Nippon Sheet Glass Co., Ltd., 10 Ω/sq) was ultrasonically cleaned with a surfactant, deionized water, acetone, and isopropyl alcohol for 20 minutes each, and treated with oxygen plasma for 5 minutes. Then, a PEDOT:PSS aqueous solution was filtered using a 0.45 µm filter, spin-coated on the FTO surface at 500 rpm for 9 seconds and 4000 rpm for 60 seconds, and then annealed at 140° C. for 20 minutes (40 to 50 nm).

Figure 2:
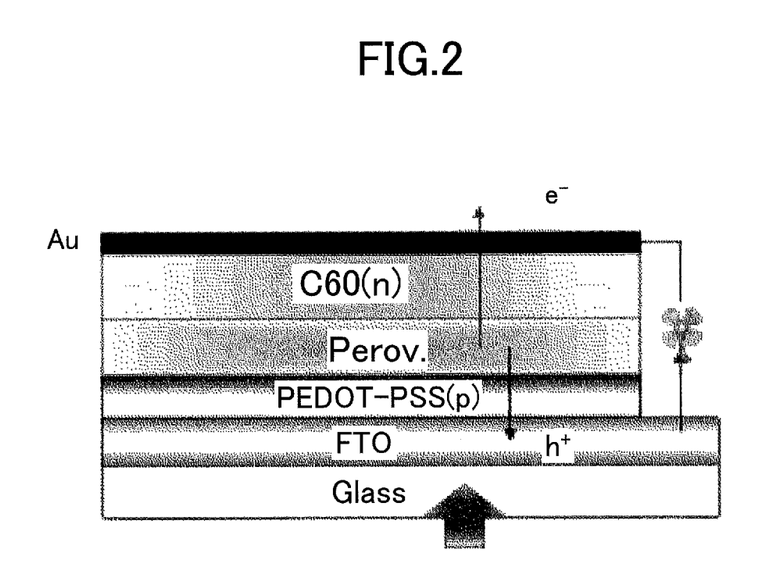
FIG. 2 is a schematic diagram of the photoelectric conversion device fabricated as Example 1.

The subsequent process was performed in a nitrogen-purged glove box ($O_2$ and $H_2O$ concentrations were maintained below 1.0 ppm and below 0.02 ppm, respectively). The prepared perovskite film was deposited on a PEDOT:PSS substrate, and a $C_{60}$ layer (50 nm), BCP (8 nm) and Au layer (100 nm) were sequentially deposited on the perovskite layer (100 to 200 nm) by thermal evaporation under vacuum through a shadow mask with an active region of 0.10 cm². FIG. 2 schematically illustrates the configuration of the produced photoelectric conversion device.

<Performance Test>

Figure 3:
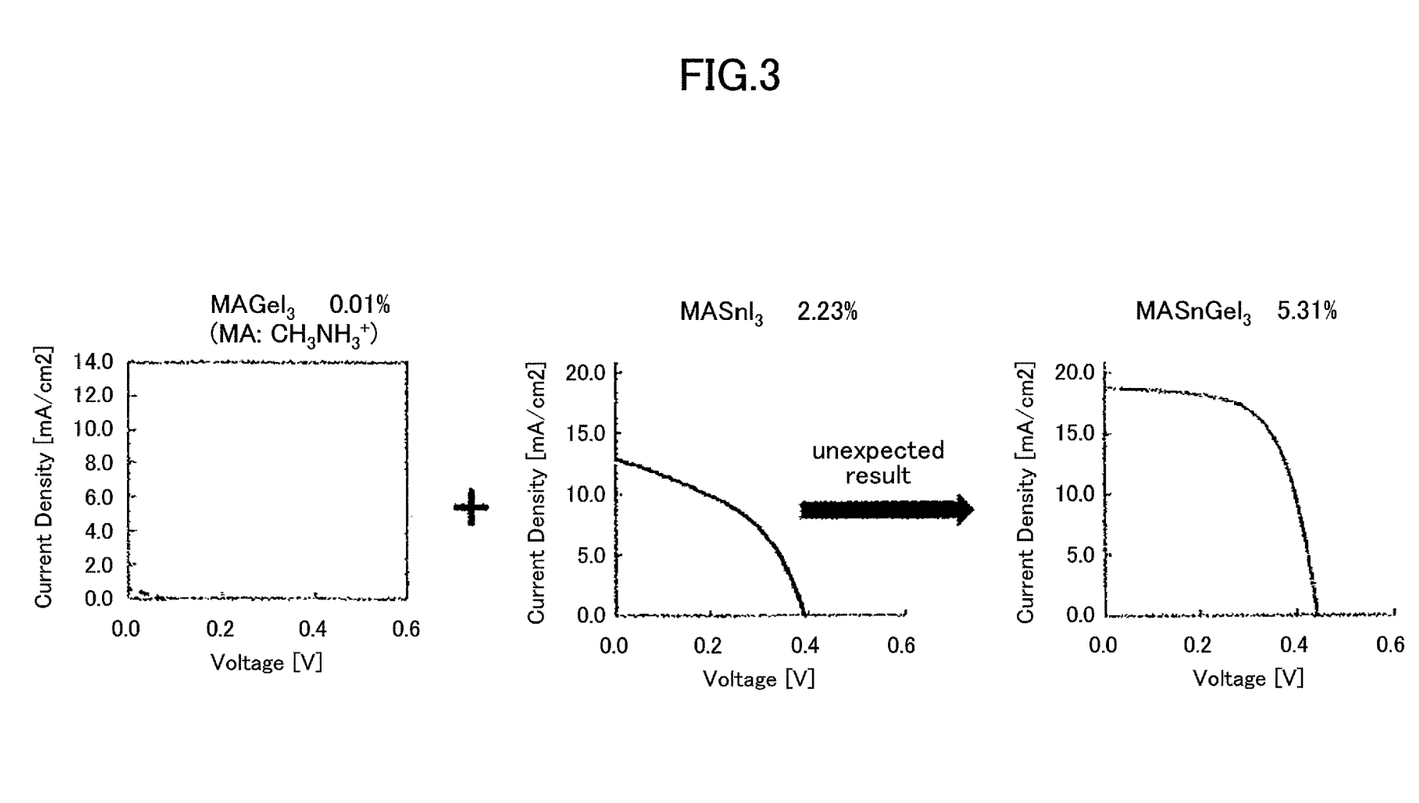
FIG. 3 is a voltage-current density curve of the photoelectric conversion device fabricated as Example 1.

The output characteristics of the photoelectric conversion device having the fabricated perovskite layer (as a photo-absorption layer) were investigated. Specifically, using a solar simulator (CEP-2000SRR manufactured by Spectrometer Co., Ltd.), the voltage-current density curve of the produced photoelectric conversion device was acquired, and then the conversion efficiency (%) was determined. The conversion efficiency (%) of the photoelectric conversion device is calculated by dividing the value [Jsc (A/cm²)×Voc (V)×FF (%)] by the incident light intensity. FIG. 3 shows the voltage-current density curve of the photoelectric conversion device.

The conversion efficiency of the photoelectric conversion device having the $MASnGeI_3$ perovskite layer of Example 1 that contains the combination of Sn and Ge was 5.31%. This conversion efficiency is greatly improved, compared with the photoelectric conversion device having the $MASnI_3$ perovskite film (Comparative film 1) with Sn alone at the B site, which exhibits the conversion efficiency of 2.23%, or the photoelectric conversion device having the $MAGeI_3$ perovskite film (Comparative film 2) with Ge alone at the B site, which exhibits the conversion efficiency of 0.01%.

Example 2

Similarly to Example 1, a photoelectric conversion device using the perovskite compound $NH_2CH=NH^{2+}CH_3NH_3SnGeI_3$ ($FAMASnGeI_3$) of the invention was prepared and its characteristics were evaluated. In Example 2, the composition ratio of Sn and Ge was changed and the influence thereof was investigated.

<Preparation of Perovskite Film>

Deposition of the perovskite film was performed in the nitrogen-purged glove box. An $FAMASnI_3$ precursor solution was prepared by dissolving $SnI_2$ (596 mg), $SnF_2$ (25 mg), and FAI (206 mg) and MAI (64 mg) in DMF (1773 µL) and DMSO (227 µL). An $FAMAGeI_3$ precursor solution was also prepared by dissolving $GeI_2$ (131 mg), FAI (52 mg) and MAI (16 mg) in DMF (500 µL). Finally, the $FAMASnI_3$ and $FAMAGeI_3$ precursor solutions were mixed at a volume ratio of (1−x):x to obtain $FAMA(Sn)_{1-x}(Ge)_xI_3$ solutions (x=0, 0.05, 0.1 and 0.2).

The precursor solution was filtered using a 0.2 µm filter and spin-coated on the substrate (PEDOT:PSS) at 5000 rpm for 50 seconds. In the spin coating process, toluene acting as an antisolvent was dropped onto the substrate before the perovskite solution was completely dried in order to flatten the surface of the perovskite. After completion of the spin coating, all the perovskite films fabricated were annealed on a hot plate at 70° C. for 10 minutes. The compositions of the prepared perovskite films were $(FA)_{0.75}(MA)_{0.25}(Sn)_{1-x}(Ge)_xI_3$ (x=0, 0.05, 0.1, and 0.2, namely, Ge contents were 0%, 5%, 10%, and 20%).

<Device Fabrication>

An ITO-coated glass substrate (Nippon Sheet Glass Co., Ltd., 10 Ω/sq) was ultrasonically cleaned with a surfactant, deionized water, acetone, and isopropyl alcohol for 20 minutes each, and treated with oxygen plasma for 5 minutes. A PEDOT:PSS aqueous solution was filtered using a 0.45 µm filter, spin-coated on the ITO surface at 500 rpm for 9 seconds and 4000 rpm for 60 seconds, and then annealed at 140° C. for 20 minutes (40 to 50 nm).

Figure 4:
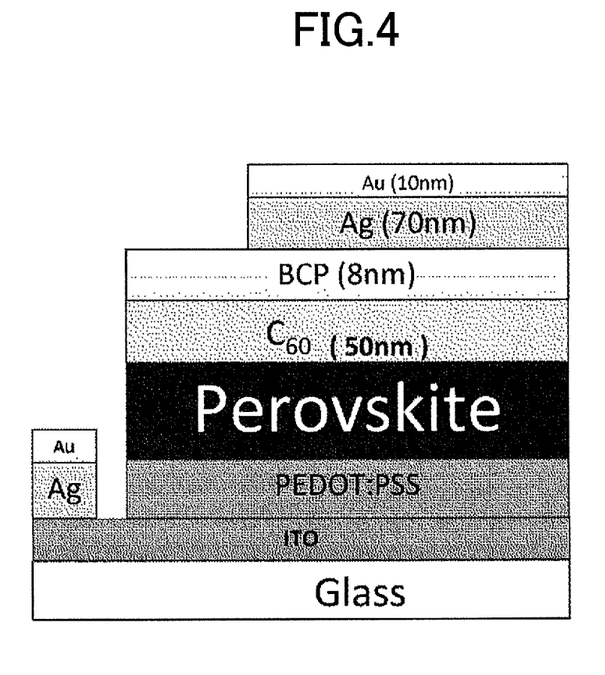
FIG. 4 is a schematic diagram of a photoelectric conversion device fabricated as Example 2.

The subsequent process was performed in a nitrogen-purged glove box ($O_2$ and $H_2O$ concentrations were maintained below 1.0 ppm and below 0.02 ppm, respectively). The prepared perovskite film was deposited on a PEDOT:PSS substrate, and a $C_{60}$ layer (50 nm), BCP (8 nm), Ag layer (70 nm) and Au layer (10 nm) were sequentially deposited on the perovskite layer (100 to 200 nm) by thermal evaporation under vacuum through a shadow mask with an active region of 0.10 cm². FIG. 4 schematically illustrates the configuration of the produced photoelectric conversion device.

<Performance Test>

The output characteristics of the fabricated photoelectric conversion device having a photo-absorption layer comprised of a perovskite compound represented by $(FA)_{0.75}(MA)_{0.25}(Sn)_{1-x}(Ge)_xI_3$ were investigated. Specifically, a solar simulator (CEP-2000SRR manufactured by Spectrometer Co., Ltd.) was used to determine the conversion efficiency, open circuit voltage, short circuit current density, fill factor, series resistance, and parallel resistance at each of the Ge concentrations. The results are shown in FIG. 5.

Figure 5:
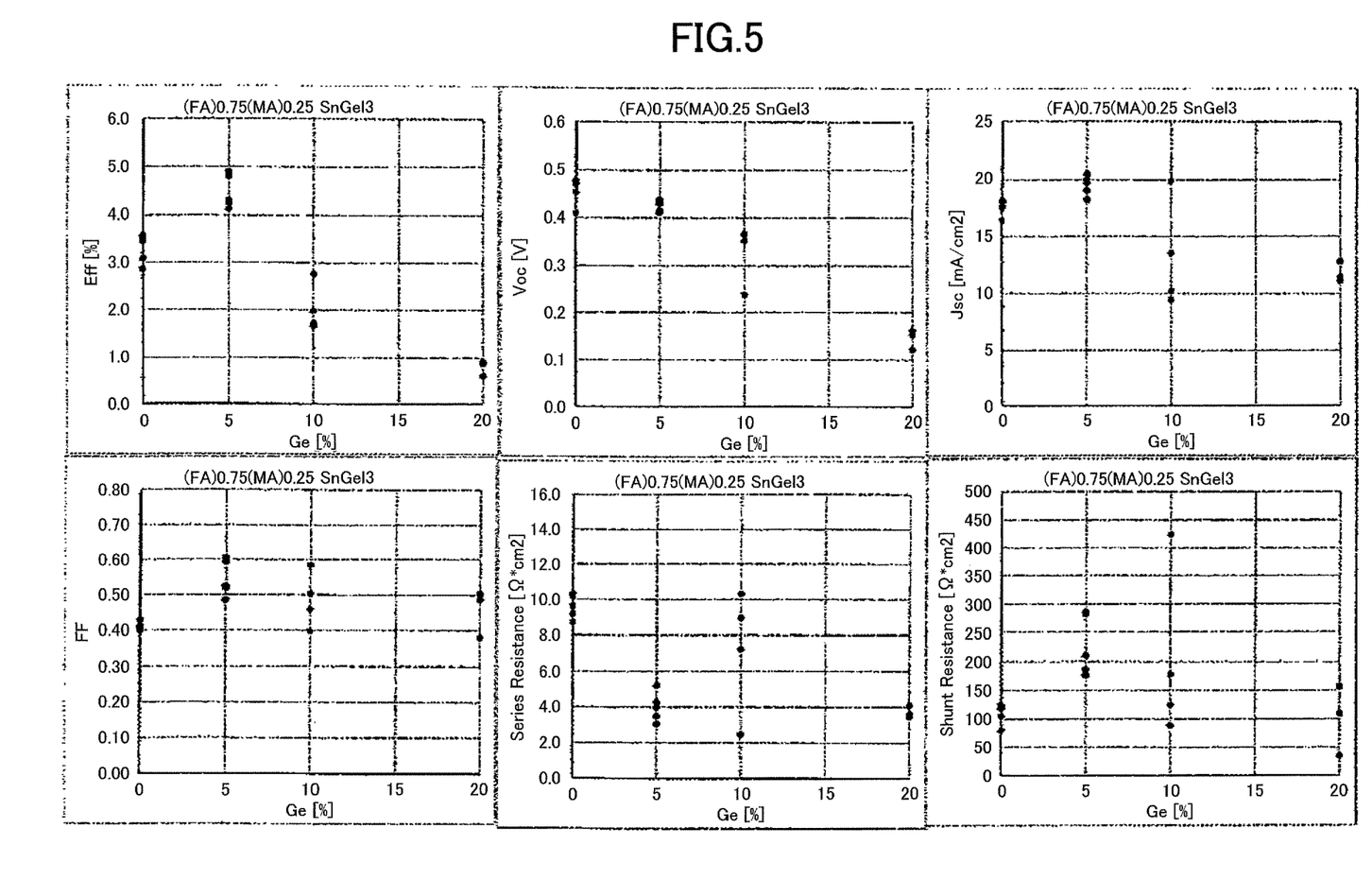
FIG. 5 illustrates the conversion efficiency (the top left), the open-circuit voltage (the top middle), the short-circuit current density (the top right), the fill factor (the bottom left), the series resistance (the bottom middle), and the parallel resistance (the bottom right) of the photoelectric conversion device fabricated as Example 2.

As shown in FIG. 5, the open-circuit voltage Voc was highest at Ge0%, but the other parameters are the most improved at Ge5%. It may be concluded that the Ge5% composition achieves the highest photoelectric conversion efficiency.

Example 3

A photoelectric conversion device was fabricated using the perovskite compound $(FA_{0.75}MA_{0.25}Sn_{0.95}Ge_{0.05}I_3)$ of the invention in the same manner as in Example 2.

<Photoelectric Conversion Efficiency in the Air>

Investigation was made with respect to a change in the photoelectric conversion efficiency occurring when the fabricated photoelectric conversion device was left in the open air. The result is shown in FIG. 6.

Figure 6:
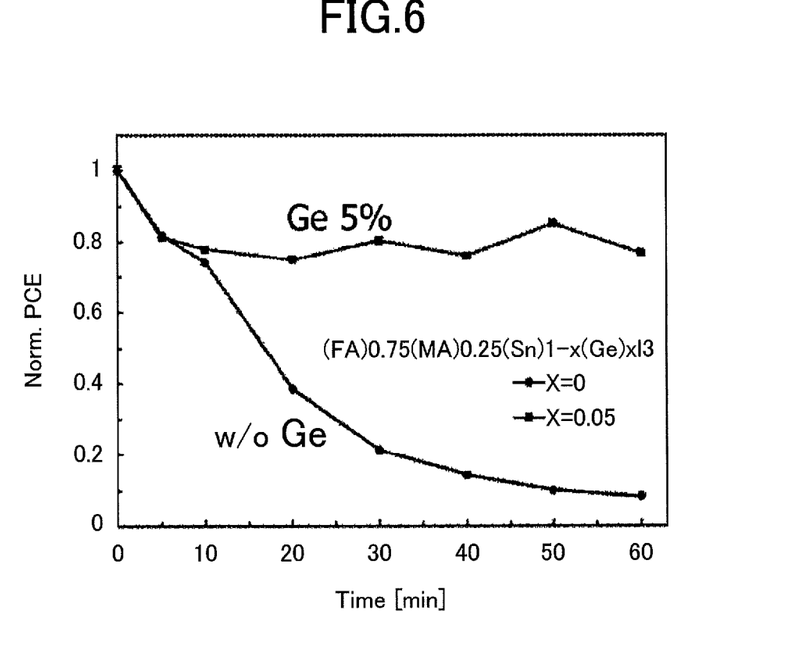
FIG. 6 is a diagram showing a change in photoelectric conversion efficiency when the photoelectric conversion device fabricated in Example 3 is left in the open air.

As shown in FIG. 6, for the photoelectric conversion device using a perovskite compound $(FA_{0.75}MA_{0.25}SnI_3)$ that does not contain Ge, the photoelectric conversion efficiency decreased to about 10% when left in the open air for 60 minutes. In contrast, it is clearly understood that the photoelectric conversion device using the perovskite compound containing Ge $(FA_{0.75}MA_{0.25}Sn_{0.95}Ge_{0.05}I_3)$ of the invention can maintain the photoelectric conversion efficiency at about 80% even after the device is left in the open air for 60 minutes.

Example 4

A photoelectric conversion device was fabricated using the perovskite compound $(FA_{0.75}MA_{0.25}Sn_{0.95}Ge_{0.05}I_3)$ of the invention in the same manner as in Example 2.

<Profile Analysis of Elements>

Cross-sectional profile element analysis was performed on the perovskite layer (photo-absorption layer) of the fabricated photoelectric conversion device, using a high-angle annular dark-field scanning transmission electron microscope (HAADF-STEM). The result is shown in FIG. 7.

Figure 7:
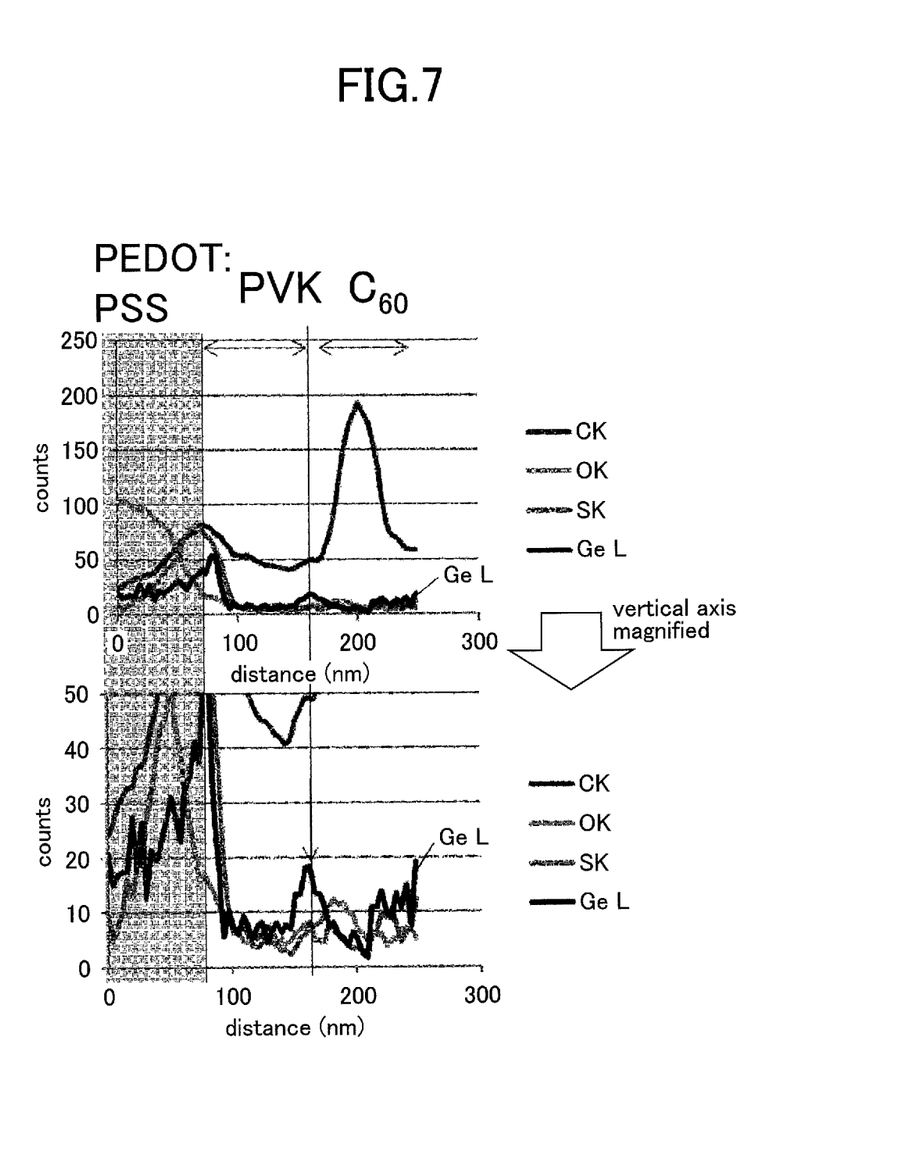
FIG. 7 shows a cross-sectional element profile analysis result of the photoelectric conversion device fabricated in Example 4, by high-angle annular dark-field scanning transmission electron microscopy (HAADF-STEM)

As shown in FIG. 7, it is revealed that Ge is localized at the interfaces of the perovskite layer. In particular, it can be seen that Ge is localized at the interface with the PEDOT:PSS layer (hole transport layer).

Example 5

Figure 8:
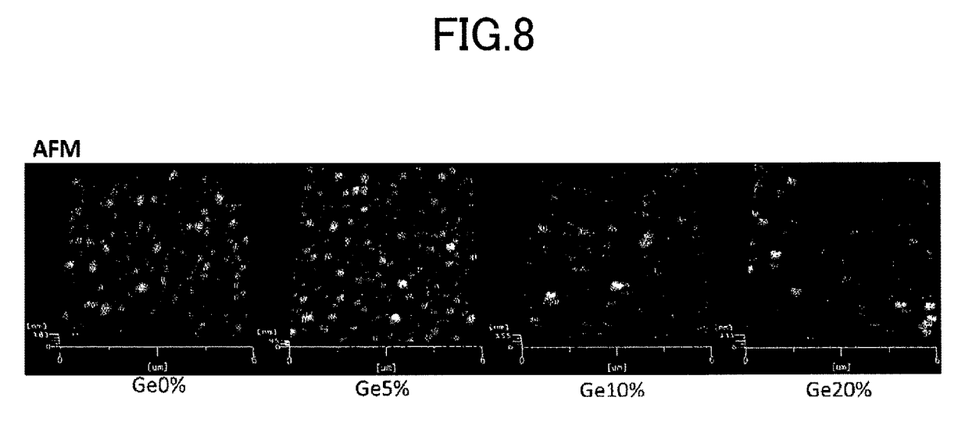
FIG. 8 is an atomic force microscope (AFM) image, observing the surface state of the perovskite compound layer fabricated in Example 5.

A layer comprised of a perovskite compound represented by $(FA)_{0.75}(MA)_{0.25}(Sn)_{1-x}(Ge)_xI_3$ (x=0, 0.05, 0.1 and 0.2, namely, Ge content of 0%, 5%, 10% and 20%) was deposited on a PEDOT:PSS substrate. The surface state of the perovskite layer was observed using an atomic force microscope (AFM), and the surface roughness was measured for each of the compositions. The results are shown in FIG. 8 and FIG. 9.

Figure 9:
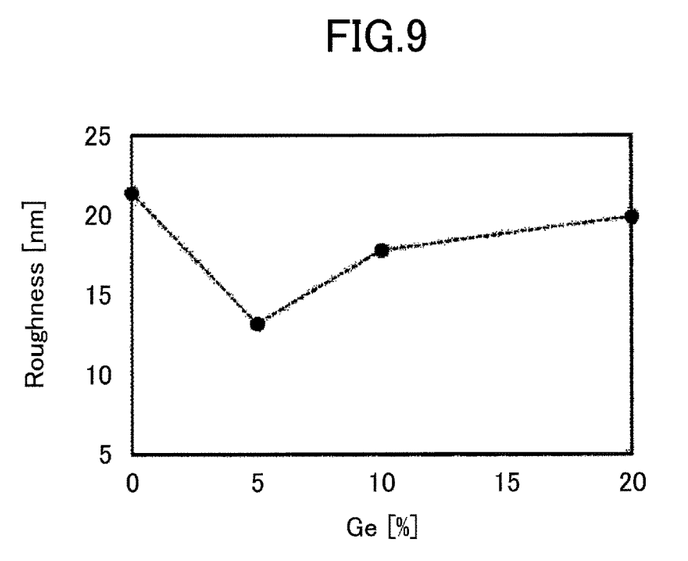
FIG. 9 shows the measurement results of the surface roughness of the perovskite compound layer fabricated in Example 5.

As shown in FIG. 9, it is understood that the surface roughness is reduced by adding Ge, and the surface roughness becomes the smallest when Ge content is 5%.

INDUSTRIAL APPLICABILITY

Photoelectric conversion devices using a perovskite compound of the present invention exhibit high photoelectric conversion efficiency, and are industrially applicable to solar cells, photosensors, and so on.

REFERENCE NUMERALS

1: photoelectric conversion device
11: substrate
12: first electrode
13: hole transport layer
14: photo-absorption layer
15: electron transport layer
16: second electrode

What is claimed is:

1. A perovskite compound represented by $ABX_3$ where A is a cation, B is a metal, and X is a halogen, each of A, B and X being composed of one or more elements,
   wherein B includes Sn and Ge,
   composition of Sn in B is 70% to 99.5% and composition of Ge B 0.5% to 30%, and
   Ge is localized at a surface of the perovskite compound.

2. The perovskite compound as claimed in claim 1, wherein the composition of Sn in B is 80% to 99% and the composition of Ge in B is 1% to 20%.

3. A photoelectric conversion device comprising:
   a photo-absorption layer containing the perovskite compound as claimed in claim 2.

4. A photoelectric conversion device comprising:
   a photo-absorption layer containing the perovskite compound as claimed in claim 1.

5. The photoelectric conversion device as claimed in claim 4, wherein the photo-absorption layer is provided between a hole transport layer and an electron transport layer, and Ge is localized between the photo-absorption layer and the hole transport layer.

6. A solar cell comprising:
   the photoelectric conversion device as claimed in claim 4.

7. A photosensor comprising:
   the photoelectric conversion device as claimed in claim 4.

8. The perovskite compound as claimed in claim 1, wherein B consists of Sn and Ge.

9. The perovskite compound as claimed in claim 1, wherein A is an organic amine or an alkali metal.

10. A perovskite compound represented by $ABX_3$ where A is a cation, B is a metal, and X is a halogen, each of A, B and X being composed of one or more elements,
    wherein B includes Sn and Ge,
    composition of Sn in B is 70% to 99.5% and composition of Ge in B is 0.5% to 30%, and
    a roughness of the perovskite compound becomes a smallest when Ge content is 5%.

11. The perovskite compound as claimed in claim 10, wherein B consists of Sn and Ge.

12. A solar cell comprising:
    the photoelectric conversion device as claimed in claim 11.

13. A photosensor comprising:
    the photoelectric conversion device as claimed in claim 8.

14. The perovskite compound as claimed in claim 10, wherein the composition of Sn in B is 80% to 99% and the composition of Ge in B is 1% to 20%.

15. A photoelectric conversion device comprising:
    a photo-absorption layer containing the perovskite compound as claimed in claim 14.

16. The perovskite compound as claimed in claim 10, wherein A is an organic amine or an alkali metal.

17. A photoelectric conversion device comprising:
a photo-absorption layer containing the perovskite compound as claimed in claim 10.

18. A peroyskite compound represented by $ABX_3$ where A is a cation, B is a metal, and X is a halogen, each of A, B and X being composed of one or more elements.
wherein B includes Sn and Ge, and
composition of Sn in B is 70% to 99.5% when A is an organic amine, and the composition of Sn in B is 90% to 99.5% when A is alkali metal.

19. A photoelectric conversion device comprising:
a photo-absorption layer containing the perovskite compound as claimed in claim 18.

20. A solar cell comprising:
the photoelectric conversion device as claimed in claim 19.

* * * * *